United States Patent [19]

Vaillancourt

[11] Patent Number: 4,525,157
[45] Date of Patent: Jun. 25, 1985

[54] CLOSED SYSTEM CATHETER WITH GUIDE WIRE

[75] Inventor: Vincent L. Vaillancourt, Livingston, N.J.

[73] Assignee: Manresa, Inc., Hillsdale, N.J.

[21] Appl. No.: 518,122

[22] Filed: Jul. 28, 1983

[51] Int. Cl.³ .................. A61M 5/00; A61M 25/00
[52] U.S. Cl. .................. 604/52; 604/165; 604/168; 604/171; 128/658
[58] Field of Search .......... 604/52, 53, 164–170, 604/171; 128/658, 772, DIG. 9, DIG. 16

[56] References Cited

U.S. PATENT DOCUMENTS

| | | | |
|---|---|---|---|
| 3,903,885 | 9/1975 | Fucas | 604/165 X |
| 4,046,144 | 9/1977 | MacFarlane | 604/168 |
| 4,326,520 | 4/1982 | Alley | 604/163 X |
| 4,417,886 | 11/1983 | Frankhouser et al. | 604/169 X |

Primary Examiner—Stephen C. Pellegrino
Attorney, Agent, or Firm—Ralph R. Roberts

[57] ABSTRACT

A catheter system is provided for the introduction and placement of a flexible catheter into the lumen of an artery or vein. A guide wire is provided and is kept in a sterile condition within a flexible bag-like enclosure attached to the hub of a needle. The needle cannula is hollow and is sharpened in the usual manner and is secured in a hub to provide a needle assembly. This hub is provided with a skirt and the cannula extends through this hub and into flow communication with a "flashback" indicator. In one embodiment the cannula is formed with a transverse hole near its interior end and in the other embodiment the cannula's inner end is in flow communication with a channel and then to a longitudinal or annular groove in a centering plug. In every embodiment there is a centering plug which provides a guideway for the guide wire which is positioned in this guideway to prevent fluid flow. The guidewire is manipulated forwardly into the lumen after penetration has been made as indicated by the "flashback". The catheter is separated from the needle hub and advanced along the guidewire until placement is achieved after which the needle, guidewire and bag are withdrawn from the patient and discarded.

23 Claims, 15 Drawing Figures

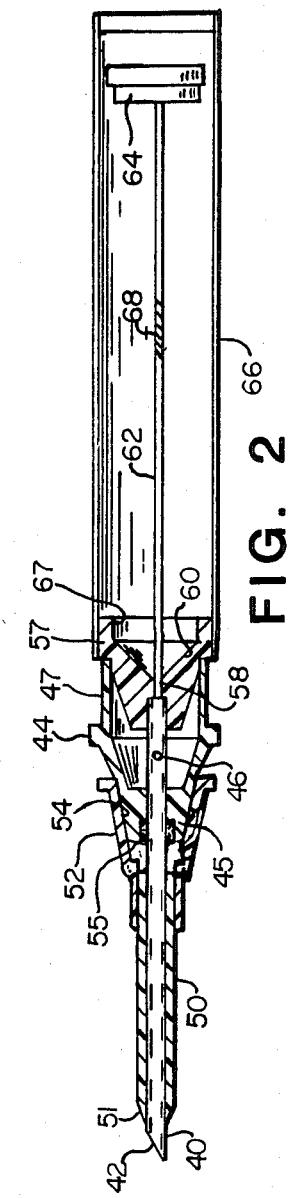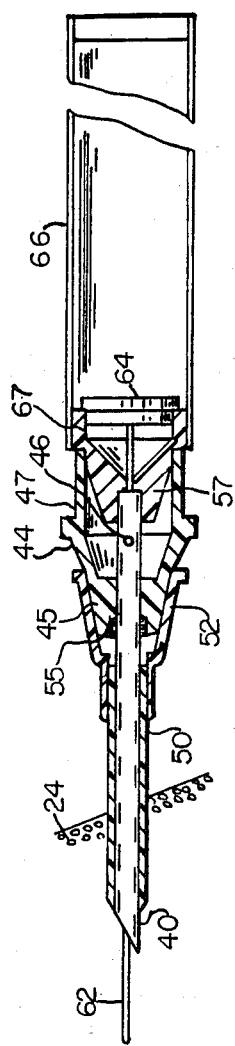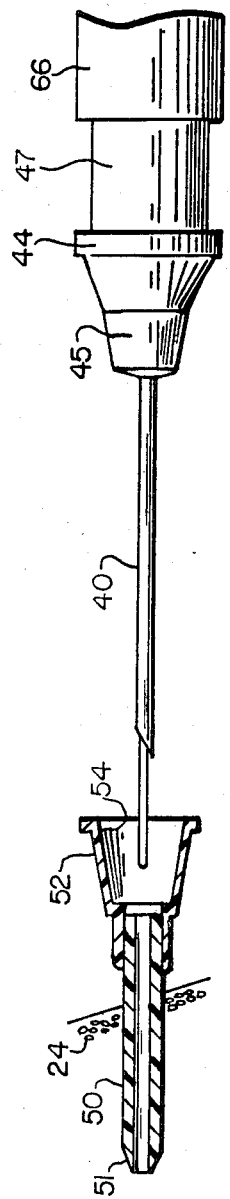

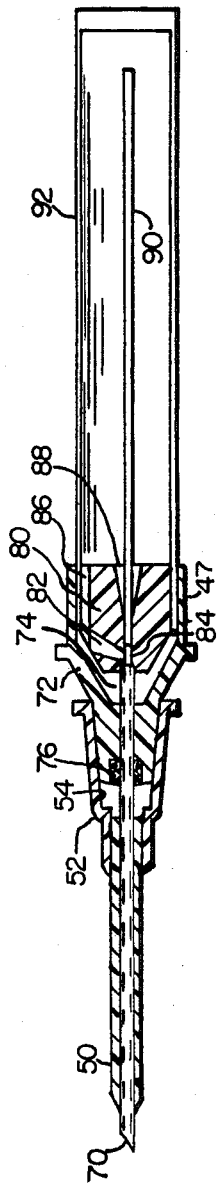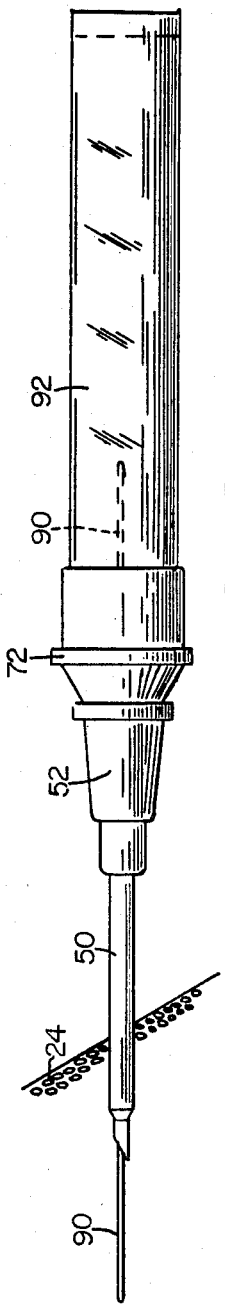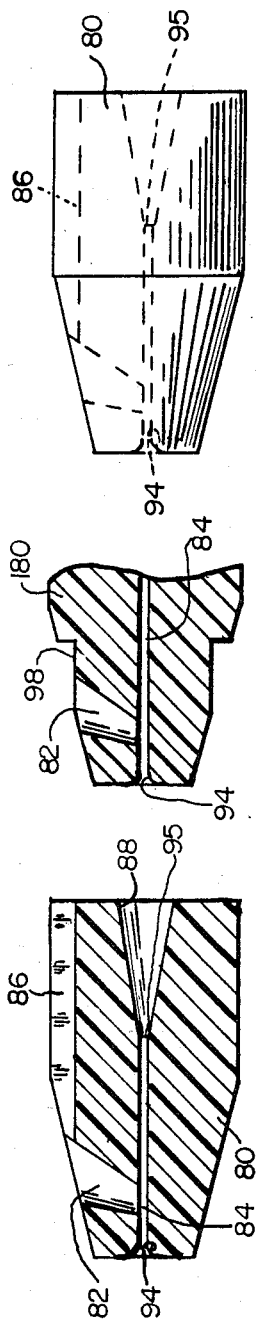

CLOSED SYSTEM CATHETER WITH GUIDE WIRE

BACKGROUND OF THE INVENTION

1. Field of the Invention

With reference to the classification of art as established in and by the United States Patent Office this invention is believed to be found in the field pertaining to "Surgery" and particularly to "flexible catheter guide".

2. Description of the Prior Art

Arterial blood infusion and withdrawal devices are known and the techniques of a guide wire inserted into the lumen of the artery is known and shown as prior art in FIGS. 1A through 1G to be hereinafter more fully discussed. A catheter placement system is shown in U.S. Pat. No. 3,416,531 to Edwards as issued Dec. 17, 1968; a guide for the catheter is also shown in U.S. Pat. No. 3,547,103 as issues to Cook on Dec. 15, 1970; a flashback indicator is shown in U.S. Pat. No. 3,942,514 as issued to Ogle on Mar. 9, 1976; a withdrawal system using a guide wire is shown in U.S. Pat. No. 4,006,743 as issued to Kowarski on Feb. 8, 1977; a catheter placement assembly is shown in U.S. Pat. No. 4,046,144 to McFarlane as issued Sept. 6, 1977; an extraction device is shown in U.S. Pat. No. 4,215,702 as issued to Mayer on Aug. 5, 1980; a blood collecting device with indicator is shown in U.S. Pat. No. 4,154,229 as issued to Nugent on May 15, 1979; a needle and sheath is shown in U.S. Pat. No. 4,230,123 as issued to Hawkins, Jr. on Oct. 28, 1980, and a guide wire placement is shown in U.S. Pat. No. 4,274,408 as issued to Nimrod on Jan. 23, 1981.

Although the present apparatus may be used in both veins and arteries, penetration into the artery is the most difficult and requires the greater expertise. The preferred arterial catheter insertion site is the radial artery immediately proximal to the wrist. This site is preferred because the artery is relatively close to the skin and therefore relatively accessible. The position and orientation of the artery is normally located by detecting the pulse and following the pulse beat up the artery for about one inch or more in length. Some practitioners draw an ink line on the skin to show this position and orientation. The catheter and needle assembly is then introduced at an angle about thirty to forty-five degrees to the surface of the skin, with the bevel of the needle facing up, or toward the outer surface.

This method of insertion is a real challenge even to the most experienced practitioner. First, he must find the artery with the point of the introducer needle and obtain flashback through the hollow of the introducer needle. Many practitioners remove the existing flash plugs in hopes of being able to obtain a quicker flashback (indication of piercing the artery). These practitioners desire a quicker flashback in the hope that this will indicate entry into the artery before penetration through the back wall of said artery with the needle point.

The artery wall is both thick (to support arterial blood pressure) and elastic and as a result the needle significantly compresses or dimples the artery wall before penetration is achieved. When the needle finally penetrates the first wall the pressure in the artery causes the wall to pop back along the needle, leaving minimal resistance to further forward travel of the needle. The most common occurrence is for the point of the needle to bury itself in the back wall of the artery when the first wall of the artery "pops" back over the heel of the bevel and along the shank of the needle. To compensate for this, some practitioners actually twist the introducer needle about its axis after they have observed flash in the introducer hub. This maneuver is intended to orient the main bevel angle parallel to the back wall of the artery and lift the embedded point out of the back wall. Other practitioners tend to draw the introducer needle back after they see flashback on the assumption that the point is embedded into the back wall of the artery.

Once the practitioner has observed flashback in the introducer and has been able to slide the catheter forward a short distance on the introducer, he assumes that he is in the artery with the tip end of the catheter. At this point, however, it is not just a simple matter of sliding the entire assembly or the catheter alone up the artery as the axis of the introducer needle is disposed at a substantial angle to the axis of the artery. This needle, when and as positioned, cannot be advanced up an artery or vessel. Rather, the practitioner utilizes a delicate feel to slide the catheter off of the introducer needle and into and up the artery. This procedure requires the advancing catheter to bend at its point of entry into the artery. Many times the catheter becomes embedded in the wall of the artery and the practitioner must detect this problem by the feel of the catheter as the catheter is slid forward. If the practitioner does not follow this procedure a substantial risk of gouging the lining of the artery and inducing a severe thrombosis occurs.

In order to get the catheter into the artery the catheter is bent so as to follow the artery. At this point the practitioner usually retracts and readvances the introducer several times during each insertion and puncture of the artery. Each placement may entail half a dozen unsuccessful attempts. Each failed attempt further aggravates the problem, because the artery goes into "spasm". After a few unsuccessful attempts, the user gives up using the catheter unit in the started attempt and with a fresh new unit begins again. In a sampling of hospitals it was found that over two needle-catheter units were used to achieve each successful catheter placement as a further indication of how difficult it is to successfully place catheters in the artery.

Although a discussion of the drawings is made in the later part of this application it is my wish to clarify the fact that FIGS. 1A through 1G represent the taught procedure which Applicant's invention seeks to make obsolete. The taught procedure in this sheet of drawings is used to achieve catheter placement in blood vessels near the heart and throat areas and may and is often used with the femoral artery. Shown in this sheet of drawings is the taught steps for inserting and using a guide wire for placing a catheter. Numbers are employed for the purpose of identification.

In FIGS. 1A through 1G the present method taught for placing a catheter, particularly in the vessels of a human, is shown. This sheet of drawings is identified as "Prior Art" and is a procedure taught in medical schools and in hospitals.

In FIG. 1A a needle 20 is carried by a body member 22 so as to be manipulated and advanced into and thorough the skin 24 of the patient. An artery or a vein 25 is depicted and the entering tip of the needle penetrates the wall of the vessel sufficiently for a flashback indication. Particularly when an artery is penetrated, blood under pressure enters and flows through the hollow needle.

In FIG. 1B the needle 20 is shown at a rather acute angle to the disposition of the vessel and further penetration of the needle may cause penetration of the opposite or rear wall as above discussed. A guide wire 20 is advanced through the bore of the needle 20 and this wire is manipulated and advanced forwardly in small increments so that the wire 27 is advanced about one inch or more in the vessel 25 to lie in said vessel as shown. This guide wire is sufficiently flexible to be bent and be advanced adjacent the rear wall of the vessel.

In FIG. 1C the guide wire 27 is shown within the vessel 25 and the needle 20 is being withdrawn from the skin and the guide wire. Care is taken so that the guide wire is not withdrawn from the artery and skin and is left in the placed position.

In FIG. 1D the guide wire 27 is still in place but the penetrated opening by the needle is not sufficient for the entrance of a catheter into the skin so a knife 29 as carried by a handle 30 is brought to and adjacent the guide wire 27. The knife 29 is manipulated to enlarge the aperture in the skin and in this enlarged opening a catheter may be advanced along the guide wire.

In FIG. 1E a catheter 32 attached to a hub 34 is first threaded along the guide wire 27 then by rotation, as indicated by the arrows, is advanced into the enlarged opening in the skin.

In FIG. 1F the catheter 32 has been advanced along the guide wire with the entering end of the catheter now in the vessel and in a bent condition in which it is to be used. Not shown is securing means for preventing dislodgement of the catheter 32 from the skin opening and vessel placement. After the desired placement has been achieved the guide wire 27, having now achieved its purpose, is removed from the placed catheter. The arrow indicates such removal.

In FIG. 1G the placed catheter 32 is shown being connected at its hub end 34 to an infusion or tubular conduit 36. A tapered end 38 is used to connect this conduit 36 to the tapered socket conventionally provided in the hub 34 of the catheter.

It is to be noted that the use of a knife 29 and the enlargement of the entering opening into the skin of the patient is usually accompanied by the loss of blood. The sterility of the entrance into the skin and the catheter used therewith is often suspect. The improved embodiments to be hereinafter more fully described avoid or minimize the difficulties of the taught method of FIGS. 1A through 1G.

This procedure has a number of significant limitations. It is a surgical procedure that is it must be performed in an operating room environment, personnel must be gowned, masked and gloved. During this procedure blood can and often does escape through the needle into the surrounding areas. This blood flow normally continues to flow around the guide wire after needle withdrawal and presents quite a challenge to the practitioner to further open the incision to allow a catheter to be placed (pushed) into the blood vessel. Unless the knife cut is just right a site for continued blood leakage is created. Many times after catheter placement the puncture area is sutured to stop leakage.

SUMMARY OF THE INVENTION

This invention may be summarized, at least in part, with reference to its objects. It is an object of this invention to provide, and it does provide, a novel and improved needle inserting device for gaining access to blood vessels, particularly arteries. The needle is hollow and is carried within a catheter secured to a hub. The needle is secured to this hub and carries within its bore a guide wire that is selectively movable. The guide wire is retained within a flexible bag so that contamination is excluded.

It is a further object of this invention to provide, and it does provide, a needle within a catheter. Said needle having a sharpened entering point by which penetration of a vessel may be and is achieved. The needle is tubular and at its rear end discharges into a flashback indicator. A thin guide wire is guided to and within the needle and there is provided wire inhibiting means to prevent unwanted movement of the wire. A flexible and impervious bag is secured to the hub carrying the needle and enclosing the wire so that a sterile field of environment is provided and needle penetration may be achieved without a need for gloves, mask, gowning, etc.

It is a further object of this invention to provide, and it does provide, an improved needle and catheter in which the catheter is carried by a hub and the needle is carried by a separate hub that is separable from the catheter hub. This needle is tubular and is disposed to carry a guide wire with inhibiting means to prevent unwanted movement of the wire while still providing a manipulative movement of the wire within the needle and/or catheter. The needle is adapted for conducting blood, after penetration of the vessel, so that an immediate flashback is detected. The guide wire is carried within and is manipulated while in a flexible and closed tubular bag attached to the needle hub.

The advantages of this catheter guide wire product include: (1) providing an entry point for a guide wire without blood leakage, (2) the advancement of the guide wire into the blood vessel under closed system (sterile) conditions, (3) the sizing by the needle of the entrance opening to the blood vessel sufficient to allow the movement of the catheter into it, (4) the advancement of the catheter into the vessel under conditions that will not injure the vessel wall and being positively guided as to where it should go, and (5) the removal of all components other than the catheter which remains in place in a sterile manner maintaining a closed system until the moment of hook-up to the pressure monitoring system, administration set, etc.

This embodiment also provides a product which is neither bulky nor cumbersome and therefore allows the practitioner to maintain control of the insertion process through feel which is a very vital part of any blood vessel (especially artery) entering procedure.

In brief, there is depicted a flexible catheter having a selected bore. The entering end of the catheter is chamfered for easy entrance of the catheter into a body opening and then into a penetrated blood vessel (artery or vein). The hub carrying the catheter has a tapered recess for receiving the feeding end of an infusion device such as is used in arterial pressure monitoring. The needle is a tubular member also fixedly secured in a hub member. This needle hub has its outer end portion sized and shaped to be seated and retained in the socket in the catheter hub. The needle has its discharge end in a side wall near this end adapted to provide a flashback indicator when the sharp needle end penetrates a vessel carrying blood.

A guide wire is provided with guide means for advancing this wire through the needle and then into the lumen, said wire bent to the configuration and path of the lumen. The guide wire is carried in a closed and flexible sheath or tube that prevents contamination of the wire and the pathway into the vessel. This flexible sheath is secured to the needle hub. The guide wire is preferably color coded to show placement advance of the guide wire to the end of the needle.

After penetration of the vessel by the needle end a flashback is perceived and the guide wire is then advanced to the end of the needle and then by careful manipulation is further advanced into the vessel. After the desired advancement into the vessel, the guide wire is used to allow the catheter to be slid along the wire generally before the needle is withdrawn from the body opening. The hub of the catheter is separated from the hub of the needle and with the wire, said needle, wire and bag are discarded leaving the catheter in place in the artery or vein.

In an alternate embodiment a modified plug provides a flashback indicator and a guide for the wire with an inhibitor means for the wire provided by mold flash.

In addition to the above summary the following disclosure is detailed to insure adequacy and aid in understanding of the invention. This disclosure, however, is not intended to cover each new inventive concept no matter how it may later be disguised by variations in form or additions of further improvements. For this reason there have been chosen embodiments of closed catheter systems with a catheter and a guide wire for placement in a lumen as adopted for use in penetration of a lumen and showing a preferred means for bending and advancing a catheter by use of a guide wire. These specific embodiments have been chosen for the purpose of illustration and description as shown in the accompanying drawings wherein:

BRIEF DESCRIPTION OF THE DRAWINGS

FIG. 2 represents a side view, partly diagrammatic and in section of a needle, catheter, flashback means, guide wire and retaining flexible bag by which the guide wire and its manipulating end button is maintained in a sterile condition;

FIG. 3 represents the assembly and apparatus of FIG. 2 but with the guide wire now advanced through the catheter;

FIG. 4 represents the assembly and apparatus of FIG. 3 but now with the needle, guide wire and retaining bag removed from the hub of the catheter, the removed members ready for discarding;

FIG. 5A represents, in an enlarged scale and in a sectional side view, a diagrammatic showing of an alternate centering plug providing a guide wire and flashback indicator, this view of only the centering plug member;

FIG. 5B represents a side view of the centering plug of FIG. 5A and showing the plug in an exterior view;

FIG. 5C represents a sectional side view, partly fragmentary, of the centering plug of FIG. 5A but showing a peripheral groove providing the flashback indicator and showing the centering plug only;

FIG. 6 represents a sectional side view, partly diagrammatic, of the assembly much like that of FIG. 2 but using the guide wire and flashback indicator of FIG. 5, and FIG. 7 represents a side view, partly diagrammatic, of the apparatus of FIG. 6 but with the guide wire advanced to guide the catheter into the vessel.

Figures 1A, 1B, 1C, 1D:
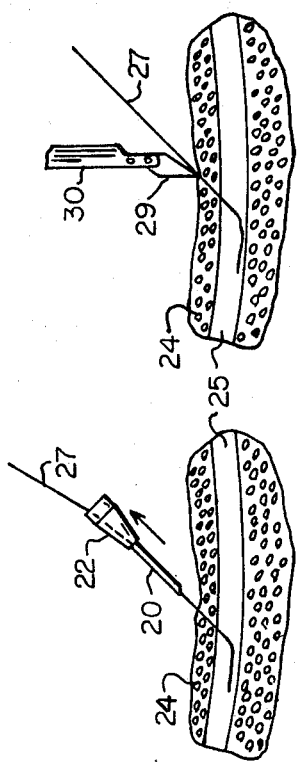
FIGS. 1A through 1G represent, in a diagrammatic manner and in side views, a step-by-step procedure now followed in using a guide wire for positioning a catheter in a blood vessel (artery or vein) and the placement therein of a catheter, this sheet of drawings is labeled "Prior Art"

In the following description and in the claims various details are identified by specific names for convenience. These names are intended to be generic in their application. Corresponding reference characters refer to like members throughout the several figures of the drawings. Structural details may be modified without departure from the concept and principles of the invention and the invention may be incorporated in other structural forms than shown.

METHOD AS TAUGHT IN FIGS. 1A THROUGH 1G

A discussion of the taught procedure of using and inserting a guide wire has been discussed with respect to the prior art. This taught procedure, as above noted, leaves much to be desired and the present invention is proposed to provide a simple guidewire placement with a closed system for a catheter used therewith.

EMBODIMENT OF FIGS. 2, 3, AND 4

In FIGS. 2, 3 and 4 there is depicted one embodiment of the closed system catheter in three stages or conditions of operation. A cannula 40 is preferably of tubular metal with its leftward and entering end beveled to provide a sharpened point 42. This cannula is secured to hub 44 which is conventionally of molded plastic and as formed has a tapered leftward extending end 45. This cannula 40 when attached to hub 44 becomes a needle assembly or in common technology a "needle". As shown, the needle assembly whose cannula extends through the hub 44 has a transverse hole or aperture 46 which provides an exit or discharge for blood passing through the hollow needle as and when the needle penetrates the wall of a vessel. This hub 44 is also provided with a cylindrical skirt portion 47 which is usually a molded portion of the hub. Conventionally this portion 47 is made transparent or at least translucent so as to indicate the presence of blood exiting from the aperture 46.

Slideable on the exterior of the cannula 40 is a catheter 50 which has a tapered entering end portion 51 which tightly engages said needle to provide a fluid seal. The remainder of the catheter bore is a slip fit to allow an easy push-off of the catheter from the cannula. The catheter 50 is secured to molded hub 52 as by cement or the like. Hub 52 is formed with a tapered female socket 54 which is a mating fit on the extending end 45 of hub 44. Cannula 40 may be secured as by cement 55 to the hub 44.

A guide plug 57 is molded and may have an air vent and is a tight fit into the interior of the skirt portion 47. This plug may be a press fit or be secured in place by cement not identified. This plug has a through passageway 58 that merges with a tapered entryway 60 extending from passageway 58 and thence outwardly toward the right end of the plug. A guide wire 62 has its left end within the cannula bore. This guide wire is slideable within the bore of the cannula 40 and on its right end has a manipulating button or stop 64. A flexible bag 66 has its left end secured to the outer right end collar portion 67 of plug 57. The other end of bag 66 is closed to provide a sterile environment within the bag. Indicia, in the form of a color band 68, may be provided on the guide wire 62 to indicate to the practitioner that the wire has been advanced to the left end of the needle 40.

USE AND OPERATION OF THE EMBODIMENT OF FIGS. 2, 3 AND 4

The inserting catheter assembly is shipped in an overwrap not shown, but of conventional construction. The skin area of the patient is prepared for a puncture to be made. The overwrap is removed and in the condition of FIG. 2 the cannula is brought to the skin 24 and the sharp end of needle 40 is caused to enter the skin. During the puncture procedure the practitioner is required to use a technique employing "feel". This technique is needed to insure that the practitioner is directing the catheter placement to an artery as above discussed. The embodiment of FIG. 2 does not interfere with the feel of the basic unit shown in FIG. 1. The needle point is advanced toward and to the arterial wall and penetration is made.

As soon as resistance to the advance of the needle point decreases and/or blood is seen in the flashback indicator the advancing of the needle 40 is stopped. The needle 40 and its transverse hole 46 enables the penetration of the vessel to be noted by the practitioner with the spurt of blood into the flashback chamber formed with and by the skirt portion 47. The flow into the chamber is noted almost immediately and it is not required that the flash chamber be filled. The practitioner moves very cautiously when flow through the needle bore is detected.

Figures 1E, 1F, 1G:
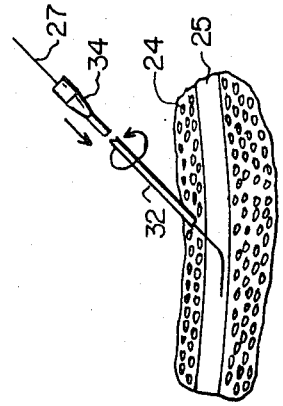

The guide wire 62 is now moved rapidly forward until the left end of the wire is at or very near the sharpened end of the needle 40. For this reason there is preferably applied to the guide wire an indicator 68 which is usually a colored band that is easily seen. The guide wire 62 is now moved forwardly with a gentle pushing action into the lumen of the artery or vein. The needle 40 has been inserted into the skin 24 at an angle such as indicated in FIGS. 1A, 1B and 3. Since the needle is disposed at an angle the guide wire bends as it is advanced up the lumen of the artery or vein. This bending and advancement of the guide wire is much like the operation seen in FIG. 1B, and this flexible wire follows the lumen 25 of the vessel.

Once the guide wire 62 has been placed in the lumen of the vessel the catheter 50 is advanced along the wire until it is fully secured within the vessel at which time the needle hub 44 is manipulated so that this hub and the hub 52 of the catheter are separated. The catheter 50 is advanced along the guide wire with the entering end curving and following the lumen of the vessel. When and with the catheter in place the needle hub 44, the guide wire 62 and bag 66 are separated as in FIG. 4, and these components are now discarded. In those cases where easy forward movement of the catheter 50 into the artery is difficult or impossible because the wall of the vessel is not totally opened, (needle beveled end 42 is not completely into the lumen of the vessel) the practitioner exerts a slight pressure on the needle 40 to effect a full penetration.

After placement of the catheter in the lumen of the vessel, usually the artery, only a small portion of the catheter 50 remains above the skin 24 as in FIG. 4. A connection to the catheter is now made using the taper 54 of the hub 52. This connection follows the procedure of FIG. 1G.

The apparatus of FIGS. 2, 3 and 4 insures that the penetration of the vessel, the advancement of the guide wire and positioning and advancement of the catheter is easily and positively achieved with only one assembly. A sterile field in and around the penetration of the needle and catheter into the skin is required but the guide wire 62 and its button 64 is retained in a protective and flexible bag 66 so that manipulation by the practitioner does not require extensive protection against contamination of those members within the bag and/or hub 44.

EMBODIMENT OF FIGS. 5A, 5B, 5C, 6 AND 7

Referring to the drawings and the embodiment of FIGS. 5A, 5B, 5C, 6 and 7, there are shown alternate embodiments to that shown in FIGS. 2, 3 and 4. As in FIG. 2, a catheter 50 is secured to a hub 52 having a receiving tapered female socket 54. A needle 70 is secured in a hub 72 which is much like the hub 44 shown in FIG. 2. This needle 70 terminates at a determined distance in from the leftward end of an interior recess 74 in the hub 72. A securing means such as cement 76 secures this needle in a desired position and extension.

In enlarged scale is shown a centering plug 80 which is depicted in FIGS. 5A and 5B. This plug has a flow channel 82 which is molded in place. This channel communicates from a center passageway 84 to a vent groove 86 formed lengthwise in the outer surface of the plug 80. An inner taper 88 is provided in this plug and is sized to provide a centering guide for a guide wire 90 particularly shown in FIG. 6. A bag 92 is retained by the plug 80 by a force fit of the plug into the recess 74. The left end of this bag 92 is shown in a secured condition in FIG. 6 and a force fit or cement may be used but this does not preclude attachment and securing of this bag exteriorally as in FIG. 3. The rear (right) end of this bag is sealed as by heat sealing but other means may be employed. The guide wire 90 is shown without a button end and without a color indicator but this also does not preclude their use. The plug 80, as it is molded, preferably has a guide taper 94 which guides the extending end of the needle 70 as it enters the plug 80. This same molding uses a diminished diameter or flash portion 95 which is deliberately created in way of the advancing guide wire and acts as a brake means to prevent unwanted movement of the guide wire 90 in the passageway 84 and the inner conduit of the needle 70. The taper 94 formed in the plug 80 is sized so as to essentially form a fluid tight seal of the plug 80 to the exiting end of the needle and a flow of blood into the center passageway 84 and then into channel and groove 86 and bag 92.

In FIG. 5C the centering plug is modified so as to provide an annular groove formed as the plug is molded. As depicted, the altered centering plug is identified as 180, the flow channel 82 is as in FIG. 5A and leads from center passageway 84 to an annular groove or step 98. This annular groove or step, when blood flows through flow channel 82 when filled, shows a band or ring indication when the skirt 47 is transparent or translucent. Groove 86 (FIG. 5A) is not present and plug 180 and bag 92 secured thereto is a tight fit so that blood does not pass into the bag 92. As in FIG. 6 the guide wire 90 is in the passageway 84 and to the right of channel 82 so as to prevent flow of blood into the bag 92.

USE AND OPERATION OF THE EMBODIMENT OF FIGS. 5A, 5B, 5C, 6 and 7

In the manner of the apparatus of FIGS. 2, 3 and 4, this needle 70 and the catheter 50 are disposed by the practitioner so as to penetrate the skin 24 of the patient.

After the desired penetration by the pointed end of the needle 70 and the catheter 50 has been advanced to penetrate the vessel as above, the guidewire is advanced into the lumen of the vessel. The guide wire bends to follow the lumen of the vessel. The advanced guide wire 90 is shown in FIG. 7. As above, the catheter 50 is advanced along the guide wire. The hub 72 is manipulated to separate the needle 70, the guide wire 90 and the bag 92 from the now placed catheter 50 and said needle and its hub, the guide wire and the bag are discarded.

The centering plug 80 seats on the rightwardly extending end of needle 70 and essentially provides a fluid-tight connection. The guide wire 90 is fed into the inner taper 88 and the mold flash or reduced portion 95 is adapted to act as a brake on the free movement of the guidewire in the passageway 84. In the initial placing condition of FIG. 6 the guide wire, although in passageway 84, is to the right of channel 82 so that blood may flow from a vessel to the end of the needle 70, through passageway 84, up channel 82 and then through groove 86 and into the interior of bag 92. Penetration of the wall of the lumen allows the flow of blood into the needle bore, thence through the channel 82 and vent 86 and brings a rapid indication of penetration to the practitioner. Advancing of the guide wire 90 effectively closes off the bore of the needle to the flow of blood so only a few drops enter the bag 92. The guide wire 90 is now advanced as above and to the condition of FIG. 7. The inner end of said wire follows the lumen of the vessel as above after which the hub 72, guide wire 90 and bag 92 are discarded and "hook-up" to a conventional inflow tubing is made.

The centering plug 180 of FIG. 5 C is anticipated as produced by molding leading to inexpensive and closely controlled manufacturing and tolerance processes. The exterior taper provided on the front or left end of the plug is sized to accommodate the hub 72 (FIG. 6). The cannula 70 extends into the recess 74 and is a friction fit on interior taper 94. An annular groove 98 is used when a hub outer skirt portion 86 is translucent or clear and the blood flowing into this groove 98 provides the desired indication. Centering plugs 80 or 180 may be made with the flow channel 82 extending to the forward wall and it is also contemplated that rather than extend into a tapered entrance 94 the cannula 70 may terminate at a determined position and the plug caused to extend forwardly so as to be in coincidence with this rear termination of the cannula. Alternate constructions may be made to provide flashback indications. Among these alternates are transverse grooves leading from the end of the cannula 70 to the skirt 86 or forward portion 72 but in all such conditions the hub or skirt is at least translucent and the guideway 84 is closed to the rear by the guidewire 90.

The centering plug is contemplated as a molding of approved plastic. The plug is made so as to provide a guideway for the guide wire. This passageway is aligned with the bore of the needle cannula so that the guide wire when and as pushed forward into the bore of the cannula readily passes into said bore. As assembly of the apparatus is usually by automatic mechanism there is provided a tapered entrance for directing the end of the guide wire into the guide way. The guide wire is inhibited in its movement by bowing the wire slightly, by providing a resilient O-ring or by deliberately producing a flash lip or portion. This inhibiting means is provided so that the guide wire is not free moving but has a small resistance to movement and that the guide wire remain in its placed position.

The bag 66 and 92 is conventionally of very thin material and is sealed at its distal end usually by heat sealing. The fore portion of this bat is secured to the hub for the needle cannula by a shrink fit, by mechanical means, by heat seal, cement or the like. It is contemplated that this bag will meet the FDA approval tests. The embodiment of FIG. 5 is usually not provided except where the hub skirt for the needle assembly is not sufficiently translucent to provide a flash back indication of penetration. It is to be noted that in FIG. 2 the rear end of the cannula 40 is inserted into the plug 57. The bag 66 is secured to the larger flange portion but this flange is merely to provide a seating shoulder for the skirt 47 and alternate constructions are contemplated. In FIG. 6 the bag 92 is secured between the outer skirt portion of hub 72 and the outer diameter of the centering plug. Other securing means as above noted may be provided and these illustrations are not considered limiting.

It is to be noted that the cannula portion of the needle is hollow and of a selected size to suit the desired use. The catheter has its entering end made as an interference fit to provide a fluid seal. The rest of the catheter is a free slip fit on the shaft of cannula. The cannula and catheter are of a length which has been selected for the particular use desired. The guide wire is of a sufficient length and flexibility to be easily advanced by the practitioner into the lumen of a vessel a desired distance so that the catheter may follow the guide wire and be positioned in the lumen of said vessel. The flash back device is coupled with a translucent or clear skirt portion associated with the needle hub. This flash back may take other forms as long as the initial flow of blood from puncturing the wall of the vessel is immediately noted after passing through the cannula.

The above catheter placing system and apparatus provides an improved method for catheter placement using a guide wire for positioning in the lumen of a penetrated vessel. This method for introducing and placing a flexible catheter into the lumen of a vessel such as an artery or vein by a practitioner includes using an advancement of a guide wire into and up said lumen and then over and along said guide wire advancing said catheter, said method including the steps of supplying a hollow needle of a determined length and sharpening an entering end of the needle and providing an exit end; securing axially a hub to said needle and at a selected distance from said sharpened end, and forming this hub with an outward and forward contoured end; providing a flash back indicator so as to be in fluid communication with or near the exit end of the needle, this flash back indicating penetration of the wall of the vessel by the sharpened end of the needle; forming a flexible catheter with a through bore and sliding this catheter on the outer diameter of the needle, and securing the rear end of the catheter to a hub formed so that its rearwardly facing end is releasably retained on the contoured forward end of the needle hub, the flexible catheter when mounted on the shank of the needle with the needle hub releaseably mounted to the catheter hub having the entering end of the catheter positioned so as to be slightly to the rear of the sharpened end of the needle; positioning a guide wire so as to be advanced to and through a guideway and into the bore of the needle and as said guide wire is advanced bending the guide wire as it enters and follows the lumen of the vessel; enclosing the guide wire in a very thin and flexible tubular sheath and securing the end of the sheath to said needle hub to provide a sterile environment as and while the guide wire is advanced to a desired placement in the lumen of the vessel, and after said placement is made separating the catheter hub from the needle hub and advancing the catheter forwardly to follow the path of the guide wire after which a discarding of the needle hub, the attached needle, the guide wire and the tubular enclosure is made and a "hook-up" of accessory tubing may be made to the catheter hub.

Although the guide wire is usually and conventionally a wound metal wire, this does not preclude the use of a small plastic member. A flexible and circular tubular cross sectioned member may also be used.

For the purpose of identification the portion 40 and 70 are metal cannulas secured to their respective hub portions usually by molding or the like. Before attaching they are identified as "cannula" and after assembly to the hub as needles. The centering plug of FIG. 2 is shouldered to provide an interference fit with skirt 47. In FIG. 2 the guide wire 62 is placed in position but is not inserted to extend in way of aperture 46 so that blood may flow as a flashback indicator to the cavity within skirt 47. In FIG. 6 the skirt 47 of hub 72 is outside of the bag 92 and the groove 86 provides a flow channel for blood and the bag 92 is sufficiently clear or translucent for an indication of flow to be observed. Guide wire 90 is mounted in guide way 84 and as shown in FIG. 6 is to the right of and transverse passageway from the end of the cannula 70 to the outer portion. The longitudinal groove 86 is used only when the hub 72 is not sufficiently translucent to indicate the presence of blood.

Terms such as "left", "right", "up", "down", "bottom", "top", "front", "back", "in", "out" and the like are applicable to the embodiments shown and described in conjunction with the drawings. These terms are merely for the purposes of description and do not necessarily apply to the position in which the flexible catheter with guide wire placement may be constructed or used.

While particular embodiments of the systems have been shown and described it is to be understood the invention is not limited thereto and protection is sought to the broadest extent the prior art allows.

What is claimed is:

1. A catheter system for the introduction and placement of a flexible catheter in and into the lumen of a blood vessel such as an artery or vein by a practitioner and using an advancement of a guide wire into said lumen to guide the catheter as it is positioned in said lumen, said catheter system including:
   (a) a hollow cannula of a determined length and having a sharpened entering end and an exit end;
   (d) a needle hub axially secured and mounted to said cannula and in an assembled condition providing a manipulable needle, said hub positioned at a selected distance from the sharpened end of the cannula, this hub having a skirt portion providing an interior cavity and open to the rear thereof, this hub having a contoured forward end;
   (c) a flashback indicating means disposed at or near the exit end of said cannula, this flashback indicating means in flow communication with said cannula to indicate an initial penetration of said wall of the vessel by a flow of blood through this cannula;
   (d) a flexible catheter that is formed with a through bore that is sized so as to be slideable on and along the outer diameter of the cannula, said catheter having an entering end tapered so as to be easily insertable with the introduction of the cannula into the lumen and with a rear end of said catheter attached to a hub, the catheter of a length so that in mounted condition on the cannula and with the hub of the catheter slideably and removably mounted on the contoured forward end of the cannula whereat the sharpened end of the cannula extends beyond the tapered entering end of the catheter, the hub of the needle being manipulated and advanced by a practitioner so that penetration of a wall of a vessel is achieved by the sharpened end of the cannula;
   (e) a centering plug within the needle hub and means for retaining said centering plug within said cavity, this plug having a small through guideway axially positioned and terminating so as to be substantially contiguous with the exit end of the cannula and in alignment with the bore of the hollow cannula;
   (f) a guide wire positioned and sized so as to be a slide fit in the guideway in the centering plug and in the bore of the cannula and disposed to be advanced by manipulation to and through said guideway and bore of the cannula and as said guide wire exits from the entering end of the cannula the advancing guide wire is bent as it enters and follows the lumen of the vessel;
   (g) inhibiting means cooperatively positioned in and with the guideway and guide wire so as to prevent accidental and unwanted advancement of the guide wire into the guideway and bore of the cannula, and
   (h) a tubular enclosure of a very thin wall and flexible and secured at one end to the needle hub and providing within said enclosure a sterile environment as and while attached to the needle hub and said guide wire is advanced, whereas and after the guide wire and catheter are advanced to the desired placement in the lumen of the vessel said needle hub and attached cannula, guide wire and tubular enclosure are separated as an array from the catheter and its hub and with said separated array now discarded.

2. A catheter system for introducing and placing a flexible catheter as in claim 1 in which the hollow cannula is sharpened by and with a bevel slope and the flash back indicator includes, at least in part, a transverse aperture formed in the cannula near the exit end thereof and to the rear of the needle hub that is away from the contoured forward end of the hub and this aperture in the cannula is opened to a flash chamber formed by said skirt portion in the rear of the needle hub.

3. A catheter system for introducing and placing a flexible catheter as in claim 2 in which the guide wire is directed toward and to a tapered entrance to said guideway formed in and extending through said centering plug.

4. A catheter system for introducing and placing a flexible catheter as in claim 3 in which the centering plug is spaced from the end of the needle hub and closes off the skirt portion of said needle hub with a sufficient skirt portion uncovered to provide a chamber which is the flash back indicator.

5. A catheter system for introducing and placing a flexible catheter as in claim 1 in which the guide wire has a button secured to and carried on the rear end of the guide wire and away from the cannula.

6. A catheter system for introducing and placing a flexible catheter as in claim 1 in which the hub for the catheter is formed with a tapered socket which is compatible with and disposed to releaseably retain a like taper formed on the contoured forward end of the needle hub.

7. A catheter system for introducing and placing a flexible catheter as in claim 1 in which the guide wire is provided with an indicia portion intermediate its ends, said indicia corresponding to a determined distance between the indicia portion and the hub of the needle, this distance corresponding to the distance needed for advancing the guide wire to the needle hub which is also the distance for advancing the guide wire to the sharpened end of the cannula.

8. A catheter system for introducing and placing a flexible catheter as in claim 1 in which said centering plug has a tapered guide merging into said through guideway for the guide wire, said centering plug having a forward end away from the tapered guide and in said forward end and in flow communication with the guideway there is formed a transverse slot which also communicates with a longitudinal vent slot formed in the outer surface of the centering plug, this vent slot open to the rear of the plug to provide a flow path for blood flowing through the cannula after penetration of the vessel.

9. A catheter system for introducing and placing a flexible catheter as in claim 8 in which the centering plug is sized so as to retain the tubular enclosure when and as a forward end of said tubular enclosure is positioned on the centering plug and said plug and said positioned tubular enclosure are sized so as to be a press fit into the rearwardly extending skirt of the needle hub, this press fit providing the desired securing means for said tubular enclosure.

10. A catheter system for introducing and placing a flexible catheter as in claim 9 in which the forward outer diameter of the centering plug is formed with a small taper to assist in the positioning and advancement of the plug, tubular enclosure and guide wire into the skirt of the needle hub.

11. A catheter system for introducing and placing a flexible catheter as in claim 8 in which the rear end of the centering plug is formed with a mold flash portion disposed to partially block the guide way and provide said means for preventing unwanted free movement of the guide wire in the centering plug and bore of the cannula.

12. A catheter system for introducing and placing a flexible catheter as in claim 8 in which the needle hub and the skirt forming the flash back indicator are made of plastic that is at least substantially translucent.

13. A catheter system for introducing and placing a flexible catheter as in claim 1 in which the centering plug is formed with an annular surface and shoulder adapted to engage and retain the skirt portion of the needle hub to provide a seal when the skirt is mounted on the centering plug.

14. A catheter system for introducing and placing a flexible catheter as in claim 1 in which the tubular enclosure is secured to the outer surface of the needle hub by means such as heat sealing, cement, shrink fit and the like sufficient to prevent unwanted contamination of the interior of the tubular enclosure during and when the guidewire is manipulated for advancement.

15. A catheter system for introducing and placing a flexible catheter as in claim 1 in which the centering plug is formed with a contoured front to and into the guideway for the guide wire, said contoured front of the guideway adapted to mate with the exiting end of the cannula so as to be in alignment with said bore of the cannula.

16. A catheter system for introducing and placing a flexible catheter as in claim 1 in which the centering plug is formed with at least one groove or annular ring which is in flow communication to the rear end of the cannula and blood is directed to and in contact with the skirt of the needle hub.

17. A method for introducing and placing a flexible catheter into the lumen of a vessel such as an artery or vein by a practitioner using an advancement of a guide wire into said lumen and then over and along said guide wire advancing said catheter, said method including the steps of:

(a) supplying a hollow cannula of a determined length and sharpening an entering end of the cannula providing an exit end;

(b) securing axially a needle hub on and to said cannula and at a selected distance from said sharpened end, and forming this hub with an outward and forward contoured end and a skirt portion in which the annular cavity open to the rear is provided, this hub and cannula providing a manipulable needle assembly;

(c) providing a flashback indicating means so as to be in fluid communication with or near the exit end of the cannula, this flashback indicating means showing a penetration of the wall of the vessel by the sharpened end of the cannula;

(d) forming a flexible catheter with a through bore and sliding this catheter on the outer diameter of the cannula, and securing the rear end of the catheter to a hub formed so that its rearwardly facing end is releaseably retained on the contoured end of the needle hub, the flexible catheter when mounted on the shank of the cannula adapted to have the needle hub releaseably mounted to the catheter hub and when so positioned having the entering end of the catheter so as to be slightly to the rear of the sharpened end of the cannula;

(e) positioning a centering plug with the needle hub and retaining said centering plug in position so that a small through guideway is axially positioned so as to terminate at or substantially at the exit end of said cannula and in alignment with the bore of said hollow cannula;

(f) positioning a guide so as to be advanced to and through the guideway of the centering plug and into the bore of the cannula and as said guide wire is advanced bending the guide wire as it enters and follows the lumen of the vessel;

(g) positioning inhibiting means in the guideway of the centering plug so as to prevent unwanted and accidental movement of the guide wire, and (h) enclosing the guide wire in a very thin and flexible tubular sheath and securing the end of the sheath to said needle hub to provide a sterile environment as and while the guide wire is advanced to a desired placement in the lumen of the vessel, and after said placement is made advancing the catheter forward over the cannula to follow the path of the guide wire until placement in the vessel is achieved followed by separation of the cannula, attached needle hub and removal of the needle hub and attached cannula, the guide wire and sheath and discarding of same.

18. A method for introducing and placing a flexible catheter into the lumen of a vessel as in claim 17 which further includes the step of securing the cannula in the needle hub so that a portion of the cannula extends rearwardly of said hub and in this extending portion of the cannula forming a transverse aperture in the wall of the cannula so as to be in flow communication with the flash back indication means.

19. A method for introducing and placing a flexible catheter as in claim 18 which further includes applying to the guide wire and intermediate its ends and at a precisely selected position an indicia band which establishes a determined distance from the sharpened end of the cannula to the rear of the secured needle hub, this distance corresponding to the distance required for advancing the guide wire so as to bring the entering end of the guide wire to the sharpened end of the cannula.

20. A method for introducing and placing a flexible catheter as in claim 17 in which the centering plug is formed with at least one radially disposed slot leading from the exiting end of the cannula to the skirt of the needle hub and providing therewith the flash back indicating means.

21. A method for introducing and placing a flexible catheter as in claim 17 which further includes forming in the centering plug a tapered guide with the larger end of the taper open to the tubular enclosure and merging this taper into the passageway in said centering plug, and forming a transverse slot in the forward portion of said centering plug and with said slot at its inner end in flow communication with the exiting end of the cannula and at the outer end in flow communication with a longitudinal groove providing a flow path for the blood flowing through the cannula after penetration of the wall of the vessel.

22. A method for introducing and placing a flexible catheter into the lumen of a vessel as in claim 21 which further includes forming the centering plug so as to retain the tubular enclosure when the plug and tubular enclosure are brought to and into a press fit in the rearwardly extending skirt portion of the needle hub and forming this centering plug with a small taper so as to assist the positioning and mounting of said centering plug in said skirt of the needle hub.

23. A method for introducing and placing a flexible catheter as in claim 17 which includes molding the centering plug so that the guideway includes a mold flash disposed to at least partially block said guideway and providing brake means which inhibits unwanted movement and advancement of the guide wire in the guideway and bore of the cannula.

* * * * *